US011246711B2

(12) United States Patent
Lefebvre et al.

(10) Patent No.: US 11,246,711 B2
(45) Date of Patent: Feb. 15, 2022

(54) HUMERAL STEM FOR A SHOULDER PROSTHESIS HUMERAL IMPLANT

(71) Applicant: SHOULDER FRIENDS INSTITUTE, Paris (FR)

(72) Inventors: Yves Lefebvre, Strasbourg (FR); Stephane Audebert, Blecourt (FR); Johannes Barth, Meylan (FR); Christophe Charousset, Paris (FR); Jerome Garret, Limonest (FR); David Gallinet, Geneuille (FR); Jacques Guery, Nevers (FR); Thierry Joudet, Libourne (FR); Arnaud Godeneche, Saint Cyr Au Mont d'Or (FR)

(73) Assignee: SHOULDER FRIENDS INSTITUTE, Paris (FR)

( * ) Notice: Subject to any disclaimer, the term of this patent is extended or adjusted under 35 U.S.C. 154(b) by 85 days.

(21) Appl. No.: 16/886,042

(22) Filed: May 28, 2020

(65) Prior Publication Data

US 2020/0289280 A1    Sep. 17, 2020

Related U.S. Application Data

(63) Continuation of application No. PCT/FR2018/052992, filed on Nov. 27, 2018.

(30) Foreign Application Priority Data

Nov. 28, 2017 (FR) ..................... 17/61302

(51) Int. Cl.
*A61F 2/40* (2006.01)
*A61F 2/30* (2006.01)

(52) U.S. Cl.
CPC .. *A61F 2/4059* (2013.01); *A61F 2002/30146* (2013.01); *A61F 2002/30828* (2013.01);
(Continued)

(58) Field of Classification Search
CPC .. A61F 2002/30146; A61F 2002/30828; A61F 2002/3083; A61F 2/4059;
(Continued)

(56) References Cited

U.S. PATENT DOCUMENTS 4,813,963 A * 3/1989 Hori ................... A61F 2/30907
                                                        623/23.35
5,152,799 A * 10/1992 Lyons .................. A61F 2/3676
                                                        623/23.32
(Continued)

FOREIGN PATENT DOCUMENTS

| EP | 0679375 | 11/1995 |
|----|---------|---------|
| FR | 2996442 | 4/2014 |
| WO | 2016094739 | 6/2016 |

OTHER PUBLICATIONS

International Search Report for International Application PCT/FR2018/052992, dated Feb. 14, 2019.

*Primary Examiner* — Alvin J Stewart
(74) *Attorney, Agent, or Firm* — Burris Law, PLLC

(57) ABSTRACT

An integral humeral stem includes a diaphyseal portion which has, orthogonal to a diaphyseal axis, an octagonal cross-section with convex rounded angles, and a metaphyseal portion in the form of a flared corolla which extends the diaphyseal portion up to a proximal face, which has, orthogonal to a central axis, an octagonal cross-section with convex rounded angles so that the humeral stem has a peripheral surface provided with eight lateral facets and eight rounded fillets which continuously extend from the diaphyseal portion to the metaphyseal portion. On the metaphyseal portion, the rounded fillets progressively widen and the lateral facets progressively narrow from the diaphyseal portion in the direction of the proximal face.

8 Claims, 5 Drawing Sheets

(52) U.S. Cl.
CPC .............. *A61F 2002/4022* (2013.01); *A61F 2002/4062* (2013.01); *A61F 2002/4077* (2013.01)

(58) Field of Classification Search
CPC ...... A61F 2002/4022; A61F 2002/4062; A61F 2002/4077; A61F 2/367
See application file for complete search history.

(56) References Cited

U.S. PATENT DOCUMENTS

| | | | | |
|---|---|---|---|---|
| 5,314,494 | A * | 5/1994 | Huiskes | A61B 17/8808 623/23.35 |
| 5,776,204 | A * | 7/1998 | Noble | A61F 2/36 623/23.35 |
| 5,888,210 | A * | 3/1999 | Draenert | A61F 2/3662 623/23.35 |
| 6,030,417 | A * | 2/2000 | Bresler | A61F 2/36 623/23.15 |
| 6,190,418 | B1 * | 2/2001 | Gerhardt | A61F 2/367 623/23.31 |
| 2005/0055103 | A1 * | 3/2005 | Badatcheff | A61F 2/36 623/22.42 |
| 2006/0190092 | A1 * | 8/2006 | Fridshtand | A61F 2/3609 623/23.35 |
| 2016/0278945 | A1 | 9/2016 | Emerick et al. | |
| 2019/0290444 | A1 * | 9/2019 | Geais | A61B 34/10 |
| 2020/0289276 | A1 * | 9/2020 | Lefebvre | A61F 2/4014 |
| 2020/0315808 | A1 * | 10/2020 | Goldberg | A61F 2/4014 |

* cited by examiner

HUMERAL STEM FOR A SHOULDER PROSTHESIS HUMERAL IMPLANT

CROSS-REFERENCE TO RELATED APPLICATIONS

This application is a continuation of International Application No. PCT/FR2018/052992, filed on Nov. 27, 2018, which claims priority to and the benefit of FR 17/61302, filed on Nov. 28, 2017. The disclosures of the above applications are incorporated herein by reference.

FIELD

The present disclosure relates to a humeral stem for a shoulder prosthesis humeral implant.

BACKGROUND

The statements in this section merely provide background information related to the present disclosure and may not constitute prior art.

In order to address anchorage, different substantially satisfactory shapes have been proposed for the humeral stem, for example with diaphyseal portions having an ovoidal or trapezoidal cross-section as known for example from the document FR 2 996 442.

However, such ovoidal or trapezoidal shapes for the diaphyseal portion necessarily continue at the level of the metaphyseal portion which will then be substantially ovoidal or trapezoidal, at the expense of a proper bearing in the resected metaphyseal portion of the humerus.

The state of the art may also be illustrated by the teaching of the document WO 2016/094739 which describes an integral humeral stem as described hereinabove, with an elongate-shaped diaphyseal portion, and a metaphyseal portion in the form of a flared corolla which extends the diaphyseal portion up to a planar proximal face.

SUMMARY

This section provides a general summary of the disclosure and is not a comprehensive disclosure of its full scope or all of its features.

The present disclosure provides a humeral stem shaped so as to allow for a proper bearing in the resected metaphyseal portion of the humerus while conferring a good stability of the diaphyseal portion in the medullary cavity of the humerus.

To this end, it provides a humeral stem for a shoulder prosthesis humeral implant, said integral (or one-piece) humeral stem comprising:

an elongate-shaped diaphyseal portion, extending according to a diaphyseal axis and shaped so as to be implanted in a medullary cavity of a humerus;

a metaphyseal portion shaped so as to bear on a resected metaphyseal portion of the humerus, wherein the metaphyseal portion is in the form of a flared corolla which extends the diaphyseal portion up to a planar proximal face centered on a central axis, said central axis being orthogonal to said proximal face and inclined with respect to the diaphyseal axis;

wherein the humeral stem according to the present disclosure is remarkable in that:

the diaphyseal portion has, orthogonally to the diaphyseal axis, an octagonal cross-section with convex chamfered angles;

the metaphyseal portion has, orthogonally to the central axis, an octagonal cross-section with convex chamfered angles;

so that the humeral stem has a peripheral surface provided with:

eight flat lateral facets which continuously extend from the diaphyseal portion to the metaphyseal portion, eight rounded fillets which continuously extend from the diaphyseal portion to the metaphyseal portion, each rounded fillet being interposed between two adjacent lateral facets;

and the humeral stem is also remarkable in that, on the metaphyseal portion, the rounded fillets progressively widen and the lateral facets progressively narrow from the diaphyseal portion in the direction of the proximal face.

Thus, the diaphyseal portion of the humeral stem according to the present disclosure allows, by its octagonal shape, for a good stability in the medullary cavity of the humerus. In addition, with its metaphyseal portion whose rounded fillets progressively widen at the expense of the flat lateral facets, this metaphyseal portion will have a substantially trunconical shape, the term "substantially" being used because the flat lateral facets are present but in a limited manner. Thanks to this substantially trunconical shape of the metaphyseal portion, the latter will allow for a perfect bearing in the resected metaphyseal portion of the humerus both on the anterior side, on the posterior side, on the medial side and on the lateral side. Moreover, another benefit of these rounded fillets in the metaphyseal portion relates to the reduction of the possibility of slitting or fracture of the cortical bone, in particular during the final introduction of the stem into its medullary cavity.

According to one feature, on the metaphyseal portion, all of the rounded fillets have, for each cross-section orthogonal to the central axis 30, a common radius of curvature and a common center of curvature placed on the central axis.

According to another feature, the lateral facets progressively narrow in the direction of the proximal face until having a proximal width smaller than or equal to 1 millimeter at the level of the proximal face, so that the rounded fillets are substantially joined so that said proximal face has a substantially cylindrical outer circumference.

In one particular form, the proximal width of each lateral facet is zero so that the rounded fillets are joined so that the proximal face has a cylindrical outer circumference.

According to a possibility of the present disclosure, on the diaphyseal portion, the rounded fillets have reduced widths in comparison with the lateral facets.

According to another possibility of the present disclosure, the metaphyseal portion is provided with a cavity open onto the proximal face, said cavity having a cylindrical perimeter at the level of the proximal face.

In another particular form, the diaphyseal portion has a distal end with a rounded general shape, wherein the lateral facets and the rounded fillets continuously extend over this distal end until meeting at an apex of the distal end.

The present disclosure also relates to a shoulder prosthesis humeral implant, comprising a humeral stem in accordance with the present disclosure, and a humeral insert fastened on the proximal face of the metaphyseal portion and having:

either a hemispherical cap shaped for articulation with a glenosphere of a glenoid implant;

or a spherical articulation head shaped for articulation on an articulation body of a glenoid implant.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 6A is a cross-sectional view of the humeral stem according to the sectional plane A-A shown in FIG. 3;

FIG. 6B is a cross-sectional view of the humeral stem according to the sectional plane B-B shown in FIG. 3.

Figure 1:
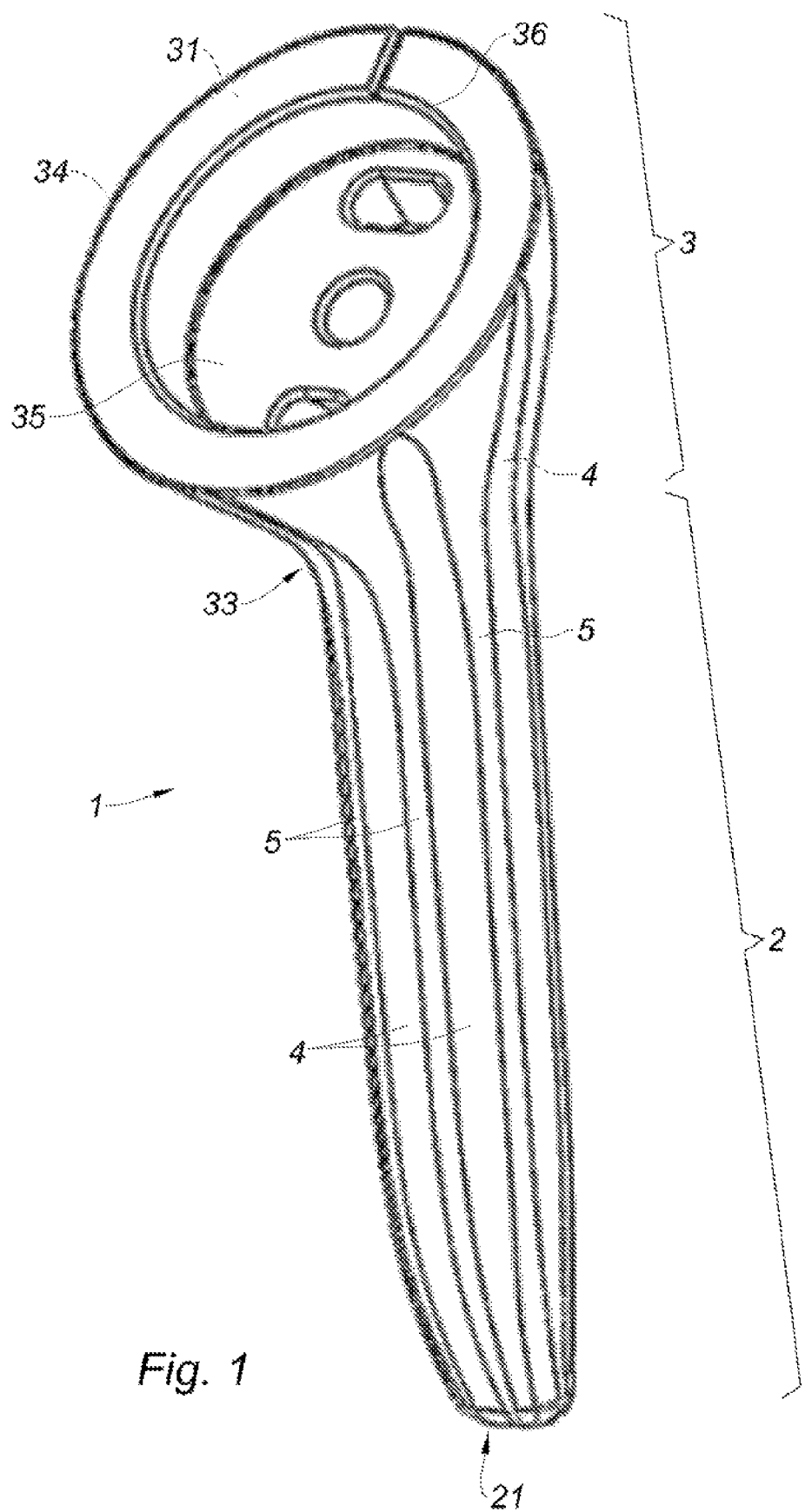
FIGS. 1, 2 and 3 are perspective views of a humeral stem according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Referring to FIGS. 1 through 6D, a humeral stem 1 comprises an elongate-shaped diaphyseal portion 2, extending according to a diaphyseal axis 20, and having a distal end 21 with a rounded shape which terminates in an apex 22. The apex 22 may be placed on the diaphyseal axis 20 or may be eccentric or offset with respect to the diaphyseal axis 20 as is the case in the illustrated form and provided as a non-limiting example.

The humeral stem 1 further comprises a metaphyseal portion 3 which is integral with the diaphyseal portion 2. This metaphyseal portion 3 is in the form of a flared corolla which extends the diaphyseal portion 2 up to a proximal face 31 (which is planar on one form) centered on a central axis 30.

This central axis 30 is orthogonal to the proximal face 31 and is also inclined with respect to the diaphyseal axis 20. The metaphyseal portion 3 has a convex lateral curvature 32 and a concave medial curvature 33 in the continuation of the metaphyseal portion 3.

The metaphyseal portion 3 is provided with a cavity 35 open onto the proximal face 31 and intended to receive a humeral insert which has:

either a hemispherical cap shaped for articulation with a glenosphere of a glenoid implant, in the case of a so-called "inverted" shoulder prosthesis;

or a spherical articulation head shaped for articulation on an articulation body of a glenoid implant, in the case of a so-called "anatomical" shoulder prosthesis.

This cavity 35 may be cylindrical or truncomical and has, in both cases, a cylindrical perimeter 36 at the level of the proximal face 31 centered on the central axis 30; such a perimeter 36 may possibly be chamfered.

Figures 4, 5:
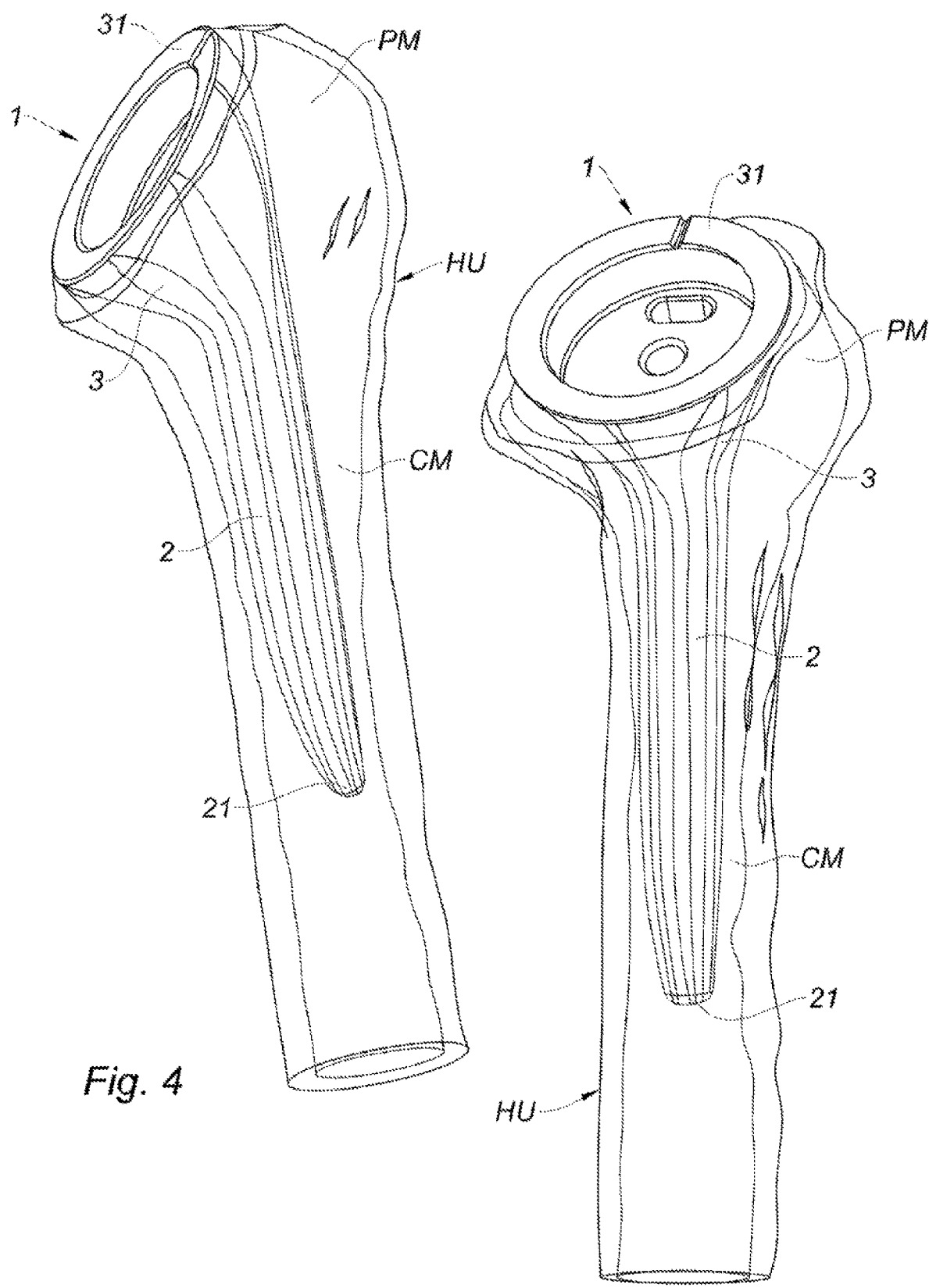
FIGS. 4 and 5 are perspective views of the humeral stem of FIG. 1 when in place in a humerus.

As shown in FIGS. 4 and 5, the diaphyseal portion 2 is shaped so as to be implanted in a medullary cavity CM of a humerus HU, whereas the metaphyseal portion 3 is shaped so as to bear on a resected metaphyseal portion PM of the humerus HU.

As regards the shapes of the diaphyseal portion 2 and of the metaphyseal portion 3:

the diaphyseal portion 2 has, orthogonally to the diaphyseal axis 20 (from the apex 22 up to the concave medial curvature 33), an octagonal cross-section with circular-arc shaped convex chamfered angles; and the metaphyseal portion 3 has, orthogonally to the central axis 30 (from the concave medial curvature 33 up to the proximal face 31), an octagonal cross-section with circular-arc shaped convex rounded angles.

Thus, the humeral stem 1 has a peripheral surface provided with:

eight flat lateral facets 4 which continuously extend from the diaphyseal portion 2 to the metaphyseal portion 3, starting from the apex 22 up to the proximal face 31; and eight rounded (or arcuate) fillets 5 which continuously extend from the diaphyseal portion 2 to the metaphyseal portion 3, starting from the apex 22 up to the proximal face 31, each rounded fillet 5 being interposed between two adjacent lateral facets 4.

Figures 2, 3:
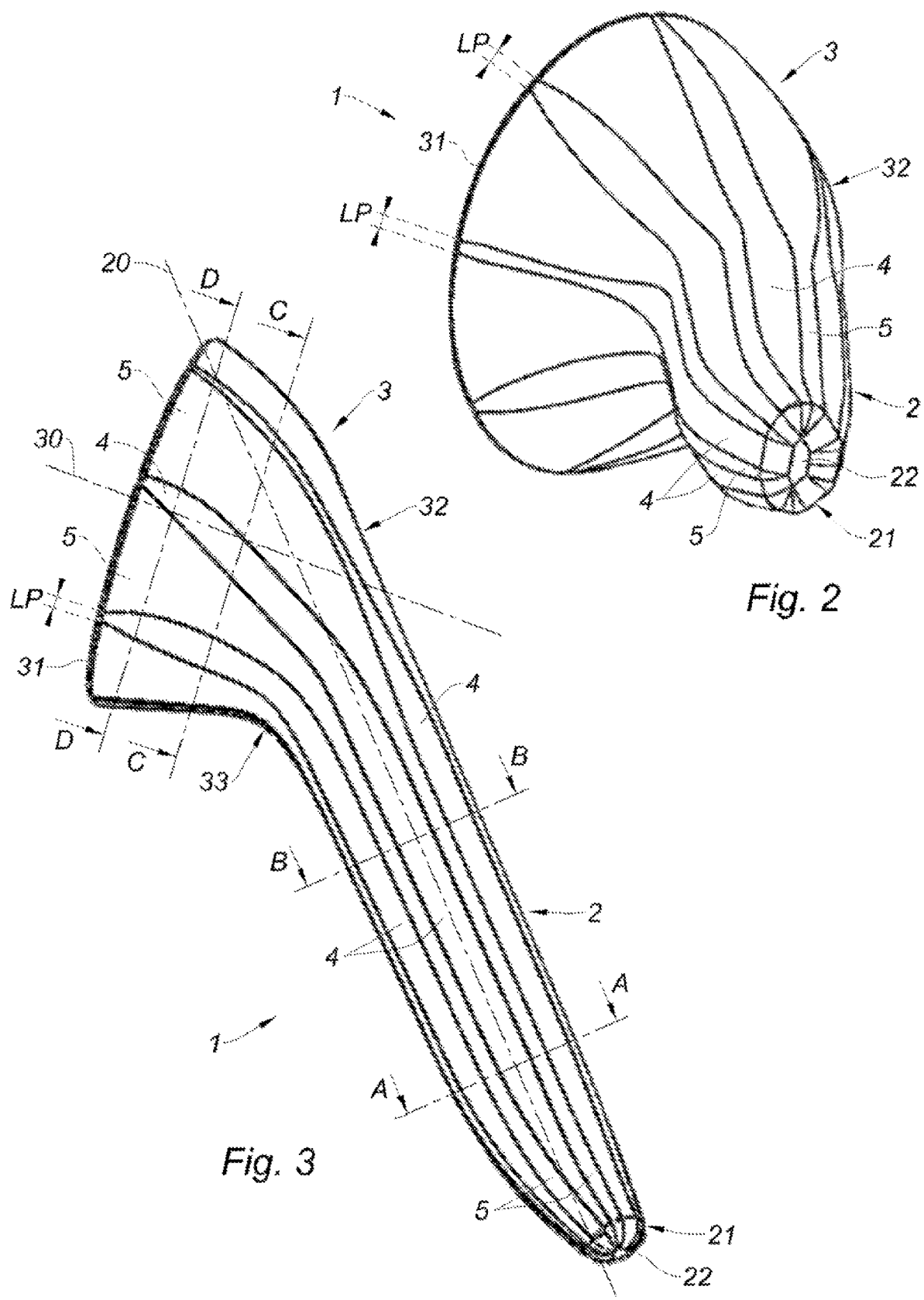

On the diaphyseal portion 2, the lateral facets 4 and the rounded fillets 5 continuously extend over the distal end 21 until meeting at the apex 22, as shown in FIGS. 2 and 3.

As shown in particular in FIGS. 6A and 6B, on the diaphyseal portion 2, the lateral facets 4 are larger than the rounded fillets 5, and the rounded fillets 5 have substantially constant widths except at the level of the distal end 21.

On the diaphyseal portion 2, the lateral facets 4 and the rounded fillets 5 narrow at the level of the distal end 21 as they get close to the apex 22, as shown in FIGS. 2 and 3, because of the tip-like shape of the distal end 21.

On the metaphyseal portion 3, all of the rounded fillets 5 have, for each cross-section orthogonal to the central axis 30, a common radius of curvature and a common center of curvature placed on the central axis 30. The radius of curvature progressively increasing from the diaphyseal portion 2 in the direction of the proximal face 31.

Figure 6C:
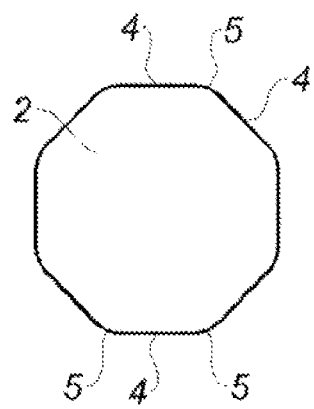
FIG. 6C is a cross-sectional view of the humeral stem according to the sectional plane C-C shown in FIG. 3.
Figure 6C:
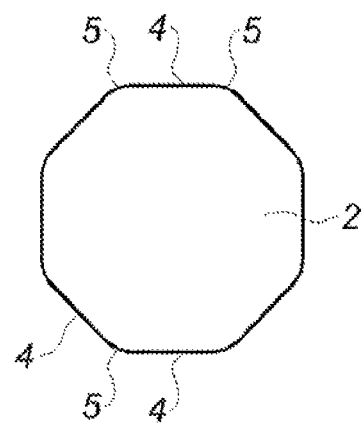
Figure 6C:
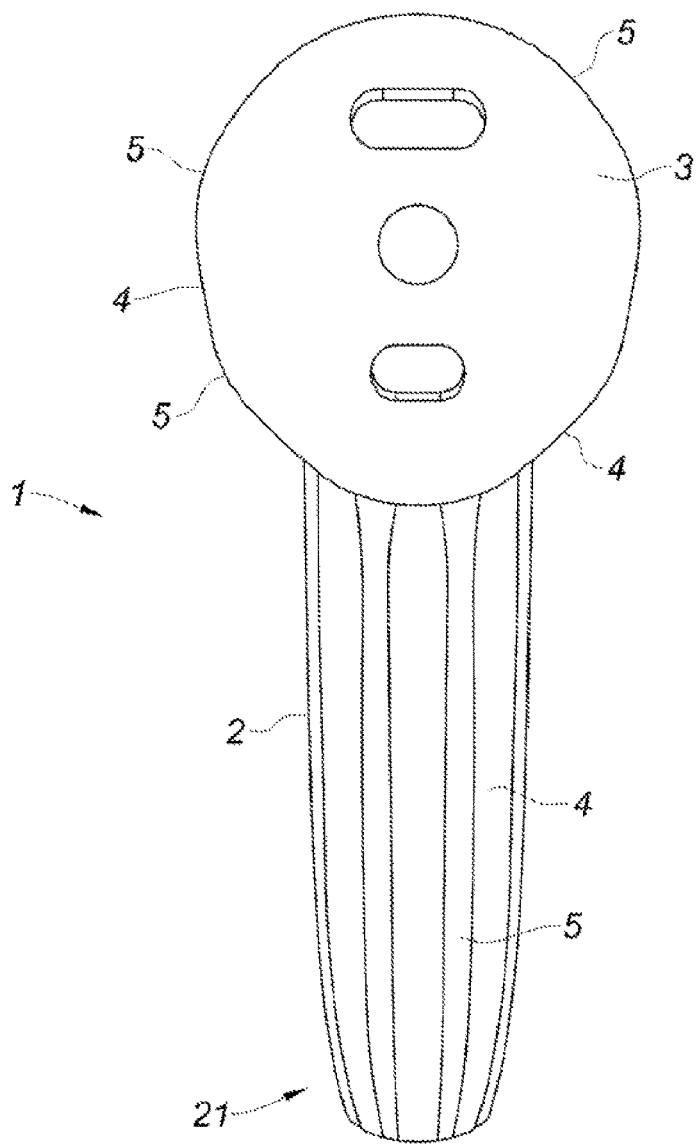
Figure 6D:
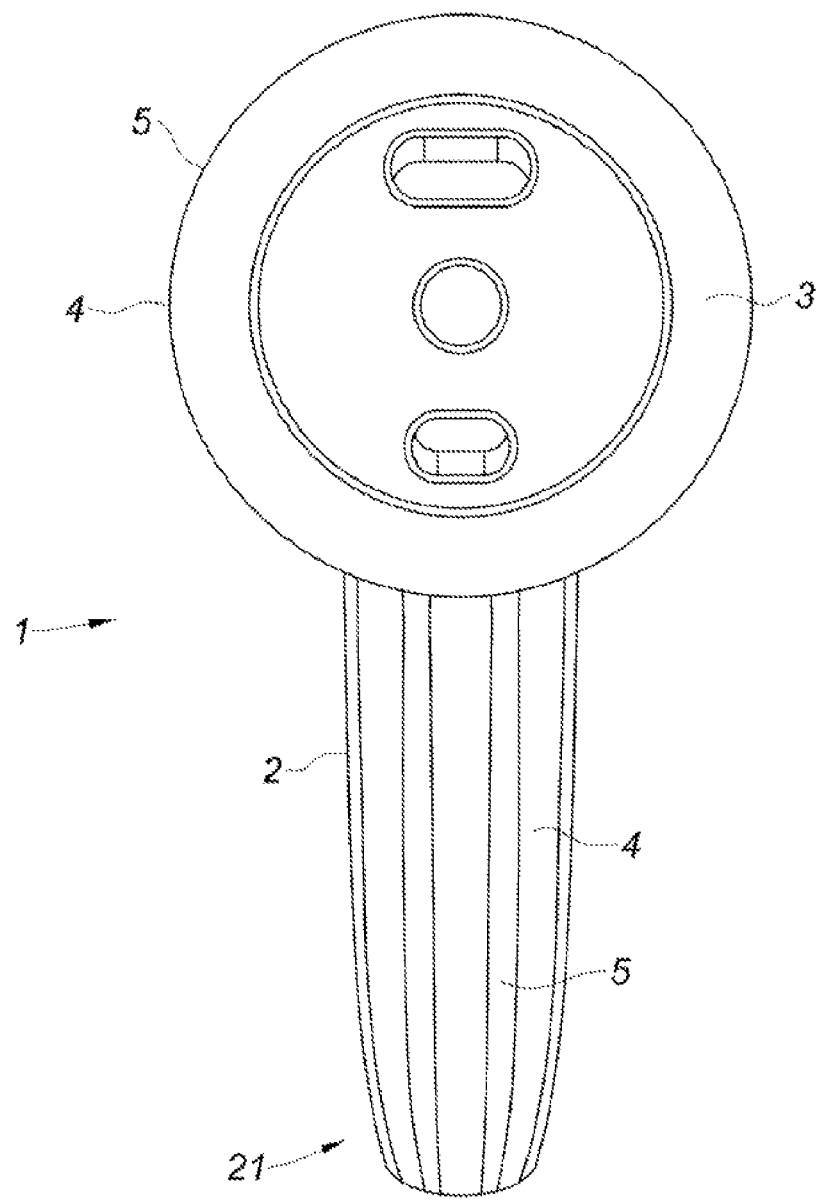
FIG. 6D is a cross-sectional view of the humeral stem according to the sectional plane D-D shown in FIG. 3.

On the metaphyseal portion 3, the rounded fillets 5 progressively widen from the diaphyseal portion 2 in the direction of the proximal face 31 and, conversely, the lateral facets 4 progressively narrow from the diaphyseal portion 2 in the direction of the proximal face 31, as shown in particular in FIGS. 6C and 6D.

More specifically, on the metaphyseal portion 3, the lateral facets 4 progressively narrow in the direction of the proximal face 31 until a proximal width LP of each lateral facet is smaller than or equal to 1 millimeter at the level of the proximal face 31, so that the rounded fillets 5 are joined (within tolerances represented by the proximal widths LP of the eight lateral facets 4) so that the proximal face 31 has a substantially cylindrical outer circumference 34 centered on the central axis 30.

It should be noted that these proximal widths LP may be zero so that the outer circumference 34 is strictly cylindrical.

Thus, the metaphyseal portion 3 has been presented hereinabove as having an octagonal cross-section with circular-arc shaped convex rounded (or arcuate) angles, which is actually the case, yet because of the widening of the rounded fillets 5 or of the narrowing of the lateral facets 4, such an octagonal cross-section with convex chamfered angles for the metaphyseal portion 3 may be assimilated to a cylindrical cross-section with eight beveled facets (in this instance the lateral facets 4). Thus, the metaphyseal portion 3 is substantially trunconical as being geometrically in the continuity of the diaphyseal portion 2.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A humeral stem for a shoulder prosthesis humeral implant, the humeral stem being integral and comprising:
    a diaphyseal portion extending according to a diaphyseal axis and elongate-shaped so as to be implanted in a medullary cavity of a humerus; and
    a metaphyseal portion shaped so as to bear on a resected metaphyseal portion of the humerus, wherein the metaphyseal portion is a flared corolla which extends the diaphyseal portion up to a proximal face centered on a central axis, the central axis being orthogonal to the proximal face and inclined with respect to the diaphyseal axis,
    wherein the diaphyseal portion has, orthogonally to the diaphyseal axis, an octagonal cross-section with convex rounded angles, and the metaphyseal portion has, orthogonally to the central axis, an octagonal cross-section with convex rounded angles, so that the humeral stem has a peripheral surface including:
        eight lateral facets which continuously extend from the diaphyseal portion to the metaphyseal portion; and
        eight rounded fillets which continuously extend from the diaphyseal portion to the metaphyseal portion, each rounded fillet being interposed between two adjacent lateral facets;
    wherein, on the metaphyseal portion, the eight rounded fillets progressively widen and the eight lateral facets progressively narrow from the diaphyseal portion in a direction of the proximal face.

2. The humeral stem according to claim 1, wherein, on the metaphyseal portion, each rounded fillet have, for each cross-section orthogonal to the central axis, a common radius of curvature and a common center of curvature placed on the central axis.

3. The humeral stem according to claim 1, wherein the eight lateral facets progressively narrow in the direction of the proximal face until a proximal width of each lateral facet is smaller than or equal to 1 millimeter at the proximal face, so that the eight rounded fillets are joined so that the proximal face has a cylindrical outer circumference.

4. The humeral stem according to claim 3, wherein the proximal width of each lateral facet is zero so that the eight rounded fillets are joined so that the proximal face has a cylindrical outer circumference.

5. The humeral stem according to claim 1, wherein, on the diaphyseal portion, the eight rounded fillets have reduced widths in comparison with the eight lateral facets.

6. The humeral stem according to claim 1, wherein the metaphyseal portion includes a cavity open onto the proximal face, the cavity having a cylindrical perimeter at the proximal face.

7. The humeral stem according to claim 1, wherein the diaphyseal portion has a distal end with a rounded shape, wherein the eight lateral facets and the eight rounded fillets extend over the distal end until meeting at an apex of the distal end.

8. A shoulder prosthesis humeral implant comprising a humeral stem according to claim 1 and a humeral insert fastened on the proximal face of the metaphyseal portion and having a hemispherical cap shaped for articulation with a glenosphere of a glenoid implant or a spherical articulation head shaped for articulation on an articulation body of a glenoid implant.

* * * * *